United States Patent [19]

Schoenwald et al.

[11] Patent Number: 4,738,851
[45] Date of Patent: Apr. 19, 1988

[54] CONTROLLED RELEASE OPHTHALMIC GEL FORMULATION

[75] Inventors: Ronald D. Schoenwald; John L. Lach, both of Iowa City, Iowa

[73] Assignee: University of Iowa Research Foundation, Inc., Iowa City, Iowa

[21] Appl. No.: 873,702

[22] Filed: Jun. 12, 1986

Related U.S. Application Data

[63] Continuation of Ser. No. 780,950, Sep. 27, 1985, abandoned.

[51] Int. Cl.$^4$ .................. A61K 9/14; A61K 31/35
[52] U.S. Cl. ................................. 424/488; 514/653
[58] Field of Search .............. 424/78, 488; 514/653

[56] References Cited

U.S. PATENT DOCUMENTS

| | | |
|---|---|---|
| 2,703,777 | 3/1955 | Feinstein et al. . |
| 3,636,200 | 1/1972 | Zentner . |
| 3,845,201 | 10/1974 | Haddad et al. ............... 424/22 |
| 3,924,004 | 12/1975 | Chang .......................... 424/358 |
| 3,937,804 | 2/1976 | Delaney et al. ............... 424/52 |
| 3,966,902 | 6/1976 | Chromecek . |
| 3,998,973 | 12/1975 | Carlson . |
| 4,003,991 | 1/1977 | Krohn et al. . |
| 4,017,598 | 4/1977 | Ohno et al. . |
| 4,018,918 | 4/1977 | Ayer et al. ................... 424/240 |
| 4,029,817 | 6/1977 | Blanco et al. . |
| 4,145,440 | 3/1979 | Fitch et al. . |
| 4,226,849 | 10/1980 | Schor . |
| 4,271,143 | 6/1981 | Schoenwald et al. . |
| 4,283,393 | 8/1981 | Field et al. . |
| 4,351,549 | 9/1982 | Dupré ........................... 524/445 |

OTHER PUBLICATIONS

Chem. Abst. 79:45753v (1973) Boyanova et al.
Chem. Abst. 79:45758a (1973) Yousef et al.
Chem. Abst. 99:76741g (1983) Rather et al.
Chem. Abst. 100:215523s (1984) Zahradnik
Schoenwald et al., "Influence of High-Viscosity Vehicles on Miotic Effect of Pilocarpine", *Journal of Pharmaceutical Sciences*, vol. 67, No. 9, pp. 1280–1283 (Sep. 1978).

*Primary Examiner*—Douglas W. Robinson
*Attorney, Agent, or Firm*—Zarley, McKee, Thomte, Voorhees & Sease

[57] ABSTRACT

An ophthalmic gel for topical application to the conjunctival sac of the eye. The gel comprises an ophthalmic drug carried in a gel which provides good ocular retention while avoiding burst release of medicament and yet at the same time providing controlled release of the medicament. The gel contains in combination sodium carboxymethyl-cellulose and colloidal magnesium aluminum silicate. A combination of these ingredients in the gel provides the desired effects.

1 Claim, 1 Drawing Sheet

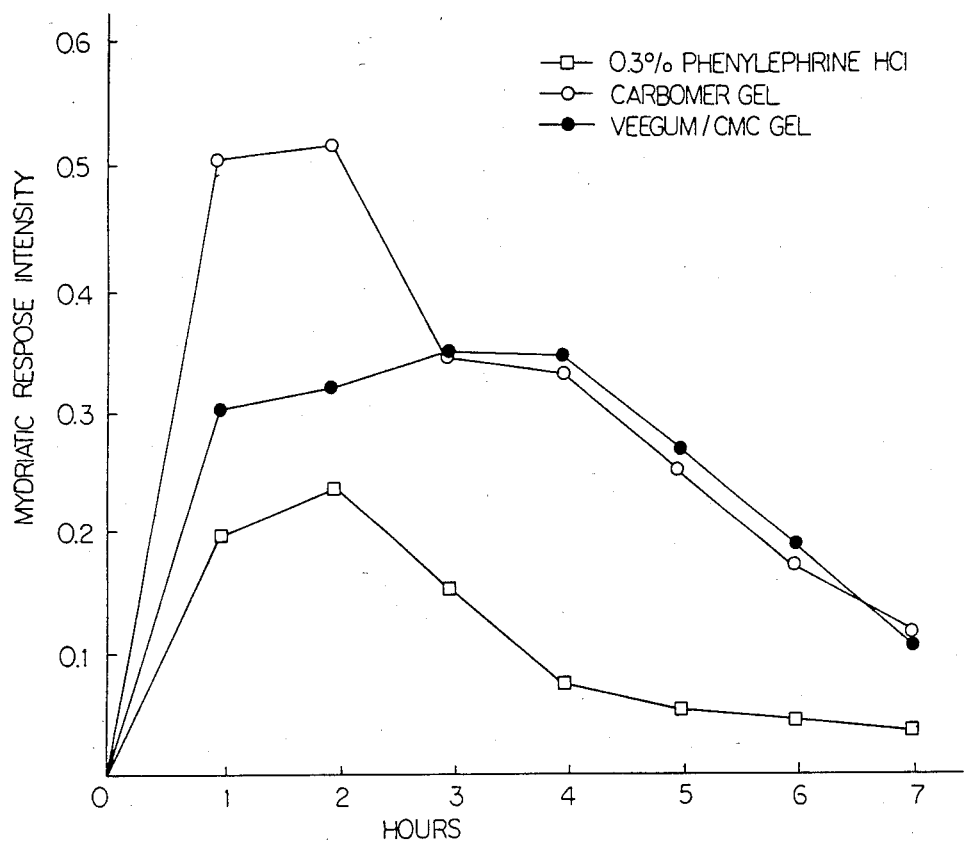

CONTROLLED RELEASE OPHTHALMIC GEL FORMULATION

This is a continuation of copending application Ser. No. 780,950 filed on Sept. 27, 1985 now abandoned.

BACKGROUND OF THE INVENTION

This invention relates to an ophthalmic gel. Various optically active medicaments have been topically applied to the eye for some considerable time. It is of course desirable to topically apply ophthalmic drugs to the eye, as opposed to other means of administration, since the drug will have less systemic side effects if applied directly to the eye. Also, the drug may well have increased activity if it can be applied at the site of use, rather than depending upon delivery in vivo such as by route of oral or injection administration. There are however problems attendant with the route of topical administration. One of those problems is the effectiveness of the ophthalmic drug permeating the cornea. Another of those problems is the ability of the drug to be maintined within the eye. There is the natural tendency of the tears to wash the drug out of the eye. This problem is magnified by movement of the eye itself and the surrounding muscle tissue of the eye socket. These movements tend to further enhance washing out of the ophthalmic drug.

Yet another problem attendant with ophthalmic delivery by topical administration is that if the drug in dosage form is thin and watery, it will often run out of the conjunctival sac of the eye before any effective delivery occurs. An even further problem can be confronted if one attempts to thicken the delivery carrier by conventional thixotropic agents, since many of those will cause eye irritation.

There is therefore a real and continuing need to develop ophthalmic gels which are comfortable in the conjunctival sac of the eye, which will not run out, and which will provide controlled drug release to the eye. The term "controlled drug release" means that the release level into the eye will be maintained at a relatively constant level over a sufficient period of time for effective administration to occur. It often happens that there is an initial burst release, or exaggerated dosage into the eye followed by a rapid drop off. This is undesirable for several reasons. First, the initial burst release has the propensity for increased side effects, since the dose is grossly exaggerated for a fleeting period of time. Secondly, a burst release is usually followed by a very low level release. This oftentimes will not provide the desired therapeutic effect. On the other hand, controlled sustained release, at a relatively constant dosage level, is desirable.

Accordingly, there is a real and continuing need for improved ophthalmic gels which provide for good ocular retention, while avoiding burst release of medicament, and yet providing controlled release of the medicament in order to provide increased delivery efficiency, and maximum therapeutic effect. One approach to this system is described in my previous U.S. Pat. No. 4,271,143, issued June 2, 1981, which relates to a carbopol gel for ophthalmic drug delivery. However, while that system is satisfactory for its preferred drug pilocarpine, the system is not satisfactory for other drugs. It does provide for sustained release over a prolonged period of time, but it also provides an initial burst release which is undesirable, particularly when used with other drug systems such as phenylephrine. The ophthalmic gel of the present invention does not provide for initial burst release and yet provides the advantages of controlled prolonged release.

The primary objective of the present invention is to provide an ophthalmic gel which provides good ocular retention while avoiding burst release and which at the same time provides controlled release of the medicament.

A further objective of the present invention is to provide an ophthalmic gel carrier which provides good ocular retention while avoiding burst release, and which provides controlled release of medicament, with the gel containing in combination sodium carboxymethyl-cellulose and colloidal magnesium silicate.

An even further objective of the present invention is to provide an ophthalmic gel for topical application which is especially adapted for use with a variety of medicaments, but most specifically adapted for use with the preferred medicament, phenylephrine.

A further objective of the present invention is to provide a stable ophthalmic gel which provides comfort to the patient when placed in the conjunctival sac of the eye.

An even further objective of the present invention is to provide an ophthalmic gel and method for using the same, which will avoid initial burst dosages of ophthalmic drug and thus decrease the risk of undesired patient side effects caused by initial burst release of drug.

The method and manner of accomplishing each of the above objectives, as well as perhaps others, will become apparent from the detailed description of the invention, which will follow hereinafter.

SUMMARY OF THE INVENTION

This invention relates to an ophthalmic gel for topical application to the conjunctival sac of the eye. It can be used with a variety of therapeutically active ocular medicaments, but is preferred for use with mydriatic agents such as phenylephrine. The gel carrier provides for good ocular retention, avoids burst release of medicament, is comfortable in the conjunctival sac, and at the same time provides controlled release of the medicament, thereby avoiding potential risk of side effects caused by initial burst dosages. The gel contains in combination sodium carboxymethyl-cellulose and colloidal magnesium aluminum silicate.

BRIEF DESCRIPTION OF THE DRAWINGS

FIG. 1 shows a comparison of mydriatic response intensity of 0.3% phenylephrine HCl, formulated as a Solution ( -□- ), Carbomer gel, the composition of my prior U.S. Pat. No. 4,271,143, ( -○- ), and the composition of the present invention, signified by black dots ( -●- ).

DETAILED DESCRIPTION OF THE INVENTION

Generally, the present invention relates to an opthalmic gel composition which successfully delivers a variety of ophthalmic medicaments or drugs to the eye of the patient. To be successful for sustained release in the eye, a carrier composition needs to provide good eye retention, sustained release, avoid initial burst release, and of course needs to be non-toxic. Because of blinking, tearing and drainage out of the eye, materials that could be used at other sites in the body, particularly oral, are not effective as sustained release ophthalmic products. The desired eye retention is much more difficult of a problem to overcome than providing sustained release. It is a unique problem to the eye and is often the reason that many possible materials suggested for use fail as ophthalmic sustained release agents. My own prior U.S. Pat. No. 4,271,143 contains carbomer, which was found desirable as a sustained release agent for pilocarpine. The composition of this present invention is superior to my prior patent in that it avoids initial burst release of the drug and is a composition of a more rigid nature. When the ophthalmic gel of this invention is prepared using the combination of sodium carbosymethyl-cellulose and colloidal magnesium aluminum silicate, at the concentrations hereinafter specified, the gel is rigid enough for use in the eye, and yet provides comfort. It should be mentioned that at other concentrations other than those hereinafter specified, the ingredients do not seem to provide the uniqueness of good retention, sustained release, and avoidance of initial burst release, while at the same time providing comfort. Suspensions even of these same ingredients at different levels which flow and are not rigid are not useful. Thus, any prior oral suspensions containing sodium carboxymethyl-cellulose and colloidal magnesium aluminum silicate, not at the levels specified herein, but at levels for oral administration, flow and would not work, in the context of this invention. In this regard, see for example Zentner U.S. Pat. No. 3,636,200.

The gel carrier of this invention contains in combination amounts of sodium carboxymethyl-cellulose and colloidal magnesium aluminum silicate at levels which provide the above-described desired results. Generally those levels will be within the range of from about 0.5% by weight of the gel to about 3.0% by weight of the gel of sodium carboxymethyl-cellulose and from about 2.0% by weight of the gel to about 4.5% by weight of the gel of colloidal magnesium aluminum silicate. Sodium carboxymethyl-cellulose is a known material, readily commercially available. Sodium carboxymethyl-cellulose useful in this invention can be obtained from a variety of sources, but one which is preferred is sodium CMC 7HF. It is obtainable from Hercules and has a molecular weight of about 700,000 and an average of 7 carboxymethyl groups substituted with 10 anhydroglycose units.

Similarly, colloidal magnesium aluminum silicate is a known and readily available composition. It can be obtained under the trademark VEEGUM from R. T. Vanderbilt Company, Inc. of 30 Winfield Street, Norwalk, Conn. Colloidal magnesium aluminum silicate, is derived from natural smectite clays and can be purchased as a soft white flaked product. It has a tendency to gel when it rests, but flow more freely when shaken. The preferred composition for use in this invention is sold under the trademark VEEGUM HV by R. T. Vanderbilt Company, Inc. Its chemical analysis is described in R. T. Vanderbilt Company's literature as 56.9% silicon dioxide, 13.0% magnesium oxide, 10.3% aluminum oxide, 0.8% ferric oxide, 2.0% calcium oxide, 2.8% sodium oxide, 1.3% potassium oxide, and as having an ignition loss of 12.6. VEEGUM HV has a viscosity of from about 800 centipoises to about 2200 centipoises and an aluminum magnesium ratio of from about 0.5 to about 1.2.

The ophthalmic gel formulation of the present invention has a pH within the range of from about 3.5 to about 8.5. Preferably the pH is adjusted to within the range of from about 6.5 to about 7.5. pH adjustment can be by use of conventional inorganic or organic acid materials useful in ophthalmic formulations such as hydrochloric acid, acetic acid, citric acid, sulfuric acid, boric acid, and the like.

The ophthalmic gels of this invention can as well be characterized by their yield values and their viscosity. Generally they have a viscosity of from 20,000 CPS to about 120,000 CPS. Preferably the viscosity at 0.5 sec$^{-1}$ (rate of shear; CP-52 cone) is within the range of 25,000 CPS to 60,000 CPS. The yield value is explained in my prior U.S. Pat. No. 4,271,143. It is a useful measurement for studying the rheological properties of ophthalmic gels. This is also mentioned in my prior paper Schoenwald et al, "Influence of High Viscosity Vehicles on Moitic Effect of Pilocarpine", *Journal of Pharmaceutical Science*, Vol. 67, No. 9, September, 1978, pp. 1280–83. Generally those things which have high yield values do not move easily, but once movement is begun, they can move more rapidly. In this instance, it relates to the ability of the gel to maintain its integrity while stationary, but once moved by movement of the eye against the gel in the conjunctival sac, it continues its movement. Satisfactory yield values, as measured by a Brookfield cone and plate viscometer (model HBTDCP), for the gels of these invention are between 2,000 dynes per centimeter squared and about 10,000 dynes per centimeter squared. Perhaps another way of expressing the yield value is the force necessary to get the gel to initially flow.

It is not known precisely why the combination of this invention works to provide controlled release, avoid initial burst release, comfort in the eye, and safety. It is believed that the combination of the sodium carboxymethyl-cellulose and the colloidal magnesium aluminum silicate conjunctively work together to form a gel formation with the active drug cross-linked within the gel formation.

In a preferred form, the composition of the present invention also contains a glucose polymer with an average molecular weight of about 40,000,000 in which the glucosidic linkages are predominantly of the (1→6) type. Preferred for use is the glucose polymer sold under the trademark DEXTRAN. When DEXTRAN (40,000,000–50,000,000 mol. wt.) is employed it should be used at a level of from about 0.5% to about 3.0% by weight. DEXTRAN is commercially available from Polysciences, Inc., Warrington, Penn. 18976.

In addition, other commonly used ingredients necessary to prepare a pharmaceutically safe and elegant composition may be used such as anti-bacterials, anti-fungals, anti-oxidants, preservatives and the like. Typical examples are benzalkonium chloride, chlorobutanol, methylparaben, propylparaben, BHA, BHT, and the like.

The composition of this invention is especially effective for use with mydriatics. The most preferred mydriatic is phenylephrine, which presently constitutes the best mode for use of the composition. It goes without saying, that other optically active medicaments may be able to be used such as mydriatic reversal agents, miotics, glaucoma medicaments, anti-infectives and anti-cataract agents. Phenylephrine is of course the most commonly used mydriatic. Miotic agents are pilocarpine, carbocol, phosphaline iodide, physo-stigmine, epinephrine. Anti-infectives include antibiotics and sulfas. An example of an anti-cataract agent is bendazac lysine.

The ophthalmic drug is present in the gel composition at a level effective to accomplish the purpose of the drug. Usual levels of use range from less than 0.5% up to perhaps 12%-15% by weight of the gel composition. For phenylephrine, effective levels are from about 0.25% up to about 10%.

The following examples are offered to further illustrate various features of the invention, but should be taken as illustrative only and not limiting.

EXAMPLE 1

Preparation of Phenylephrine HCl Formulations

| Solution | | |
|---|---|---|
| Each Contains | Ingredients | Amount Per Batch |
| 10.0% | L—Phenylephrine Hydrochloride, U.S.P. | 0.3 gm |
| 0.75% | KH$_2$PO$_4$ anhydrous monopotassium phosphate | 1.50 gm |
| 0.175% | Na$_2$HPO$_4$ anhydrous disodium phosphate | 0.350 gm |
| (0.01% + 10% excess) | Benzalkonium chloride, N.F. | |
| 0.85% | Methylcellulose U.S.P. 400 cps | 1.70 gm |
| qs 100% | Distilled water Fill 55 2 cc opthalmic containers | qs 200 ml |

Solution Preparation

About 120 ml of water is heated to about 80° C. to which is added the methylcellulose powder. The solution is stirred until all the powder is wetted. The heated solution is then placed in an ice bath and cooled until the methylcellulose is fully hydrated or about 45 minutes. The solution is then steam sterilized. To slightly less than 80 ml of water, each ingredient is added until dissolved. Methylcellulose solution is added to the solution containing the other ingredients while stirring. The solution is brought to 200 ml using distilled water.

| Ingredients | % (w/w) composition |
|---|---|
| Phenylephrine HCl, U.S.P. | 0.3 |
| Hydrochloric acid 1N, U.S.P. | 0.1 |
| Benzalkonium chloride, N.F. | 0.01 (+ 10% XS) |
| Colloidal magnesium aluminum silicate (Veegham HV of R. T. Vanderbilt Co., Inc.) | 3.5 |
| Sterile water for injection, U.S.P. QS | 100.0 |
| sodium carboxymethyl-cellulose (7HF of Hercules) | 1.5 |

Gel Preparation

Exactly 3.5 gm of the Veegum HV flakes is added to motar along with 5 gm portions of distilled water until approximately 30 gm of water has been added. With each addition of water the mixture is lightly triturated so that after the full addition of water has been added the Veegum is wetted. The mixture is set aside for 2 hours to allow for hydration of the Veegum. This mixture is referred to as part I.

About 40 gm of water is brought to 70° C. To the hot water is added CMC with vigorous stirring until a fully hydrated viscous gel is obtained. This gel is referred to as part II. When cool, part II is added slowly with stirring to part I until a homogeneous mixture results.

To a tared beaker 10 gm of water is added along with 0.1 ml of 1N HCl and 1 ml of 1% benzalkonium chloride. This solution is referred to as part III and is added to the homogeneous mixture composed of parts I and II. The weight of the gel should be adjusted to 99.0 gm using sterile water for injection. The last step allows for 1 gm of phenylephrine HCl be thoroughly incorporated into the gel using a low speed, relatively non-shearing mixer.

| Carbomer Gel: (Prior U.S. 4,271,143) | |
|---|---|
| Ingredients | % (w/w) composition |
| Phenylephrine HCl, U.S.P. | 0.3 |
| Sodium hydroxide 1N, U.S.P. | 30.0 |
| Benzalkonium Chloride, N.F. | 0.01 (+ 10% excess) |
| Mannitol, U.S.P. | 1.0 |
| Polysorbate 80, N.F. | 0.05 |
| Carbomer 934P, N.F. | 3.3 |
| Distilled Water QS | 100 |

Gel Preparation

A 100 gram gel product containing 0.3% (w/w) phenylephrine HCl is prepared as follows. Approximately 40 gm of water is added to a tared beaker containing 3.3 gms of carbomer 934P. The mixture is stirred vigorously and then allowed to hydrate for about 2-3 hours until a viscous, cloudy solution without lumps is obtained. Benzalkonium chloride, polysorbate 80, and mannitol are added to about 30 gms of water. Thirty gms of 1N NaOH is added to the carbomer solution to form a rigid, but clear gel. Phenylephrine HCl is added to the solution and stirred until a uniform solution is formed. The solution is then added to the gel and stirred until complete dispersion of the drug is accomplished. Water is added to bring the final weight of the gel to 100 gm.

The gel preparations were used to evaluate their effectiveness in prolonging the mydriatic resonse of phenylephrine compared to the viscous solution.

EXAMPLE 2

The right eye of a normal adult (2-3 months) New Zealand Rabbit was used to measure mydriasis. A flood of diffuse light was placed at a fixed distance from the rabbit eye. The light intensity was adjusted using a rheostat so that the predose pupillary diameter was always between 4.2 and 4.8. The pupil diameter (N=6) was measured using a calipers held at ½ inch from the rabbit's pupil with the viewers eye fixed just behind and above the light source. The pupillary diameter was measured at time zero and at hourly intervals through 7 hours. A dosing volume of 50 µl of each preparation was administered to a group of six rabbits at three day intervals until each rabbit received each preparation one time. The intensity of response was determined from the following equation:

$$I = \frac{(PD_t - PD_{t=0})}{(PD_{t=0})}$$

where, PD represents pupillar diameter and the subscript t and t=0 represent the time of measurement.

RESULTS

FIG. 1 of the drawing gives the results. Carbomer showed an initial burst effect, producing the highest peak at 1-2 hours and then declining from 2 to 7 hours. The invention preparation showed a lower, but sustained release (i.e., flat) effect from 1–4 hours. From 4–7 hours the pupillary response declined in an identical manner for carbomer Veegum/CMC preparations. The effect from the solution was less at all time intervals.

It can be seen that the invention was far more effective than an aqueous solution or than the gel of my prior invention which provided an initial burst. An initial burst dose was avoided by the composition of the present invention involving carboxymethyl-cellulose and colloidal magnesium aluminum silicate.

It therefore can be seen that the invention accomplishes at least all of its stated objectives.

What is claimed is:

1. A method for delivery of phenylephrine to the eye, which avoids significant burst dosage, and tear wash out, and at the same time provides sustained, controlled release of said phenylephrine, said method comprising:
   preparing an ophthalmic gel containing a mydriatically effective amount of phenylephrine, said gel comprising in combination from about 0.5% to about 3.0% by weight of the gel of sodium carboxymethylcellulose and from about 2.0% to about 4.5% by weight of the gel of colloidal magnesium aluminum silicate, said gel being eye tissue compatible, and
   administering said gel to the conjunctival sac of the eye.

* * * * *